(12) United States Patent
Reitz et al.

(10) Patent No.: US 6,200,984 B1
(45) Date of Patent: Mar. 13, 2001

(54) NAPHTHO-IMIDAZO PYRIDINE DERIVATIVES USEFUL IN TREATING CENTRAL NERVOUS SYSTEM DISORDERS

(75) Inventors: Allen B. Reitz, Lansdale; James J. McNally, Souderton; Pauline Sanfilippo, Chester Springs, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/166,021

(22) Filed: Oct. 5, 1998

Related U.S. Application Data

(60) Provisional application No. 60/061,234, filed on Oct. 7, 1997.

(51) Int. Cl.[7] .................. A61K 31/44; A61K 31/505; A61P 25/00; C07D 471/02; C07D 401/14
(52) U.S. Cl. ............... 514/285; 514/242; 514/245; 514/255.05; 514/256; 514/269; 514/272; 514/274; 514/275; 544/182; 544/198; 544/209; 544/212; 544/238; 544/301; 544/312; 544/316; 544/317; 544/319; 544/321; 544/323; 544/329; 544/332; 544/336; 544/407; 544/408; 544/409; 546/70
(58) Field of Search .................. 546/70; 514/285, 514/275, 274, 272, 269, 256, 245, 242, 255.05; 544/182, 198, 209, 212, 238, 301, 312, 316, 317, 319, 321, 323, 329, 332, 336, 407, 408, 409

(56) References Cited

U.S. PATENT DOCUMENTS 5,639,760  6/1997  Maryanoff et al. ............. 514/292
5,817,668 * 10/1998  Reitz et al. .................... 514/292

OTHER PUBLICATIONS

Smith and Olsen, Trends Pharm. Sci., 1995, 16, 162.
Takada, S. et al. J. Med. Chem, 1988, 31, 1738.
Mohler, H. Arzneim.–Forsch./Drug Res, 1992, 42 (2a), 211.
Haefely, W. et al., Advances in Drug Research, Academic Press, vol. 14, 1985, pp. 165–322.
Stephenson, Biochem. Journal, 1995, 310, 1–9.

* cited by examiner

*Primary Examiner*—Mukund J. Shah
*Assistant Examiner*—Brenda Coleman
(74) *Attorney, Agent, or Firm*—Ralph R. Palo

(57) ABSTRACT

A compound of the general formula I:

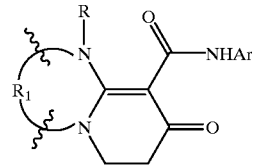

is disclosed as useful in treating disorders of the central nervous system. Pharmaceutical compositions, processes for preparing the compounds and methods of treatment are also disclosed.

17 Claims, No Drawings

NAPHTHO-IMIDAZO PYRIDINE DERIVATIVES USEFUL IN TREATING CENTRAL NERVOUS SYSTEM DISORDERS

This application claims the benefit of U.S. Provisional Application No. 60/061,234, filed Oct. 7, 1997.

BACKGROUND OF THE INVENTION

The gamma-aminobutyric acid-A receptor (GABA-A receptor) is the most abundant inhibitory receptor in the brain of mammals. It is comprised of a heteropolymeric structure that forms a chloride ion channel, and bears multiple recognition sites for the binding of modulatory molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Smith and Olsen, Trends Pharm. Sci., 1995, 16, 162; Stephenson, Biochem. J., 1995, 310,1). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. J. Med. Chem. 1988, 31, 1738). Thus BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. Arzneim.-Forsch./Drug Res, 1992, 42 (2a), 211; Haefely, W. et al., Advances in Drug Research, Academic Press, vol. 14,1985, pp. 165–322; Skolnick, P. et al., GABA and Benzodiazepine Receptors, Squires, R., Ed., 1987, pp. 99–102 and references cited therein.)

The naphtho-imidazo derivatives are a class of compounds which bind to the BZD receptor with high affinity. Most of the drugs in use are agonist-type ligands for the receptor. Such compounds are generally useful for their anticonvulsant, anxiolytic, sedative and muscle relaxant effects. Antagonists of the BZD binding site are useful for the treatment of benzodiazepine drug overdoses and inverse agonists are useful in managing alcoholism.

The present invention relates to novel compositions of matter, their use and their method of preparation. Compounds having some structural similarity to those of the present invention are described in U.S. Pat. No. 5,639,760 which is assigned to the assignee of the present invention.

SUMMARY OF THE INVENTION

The present invention is directed to compounds of the following formula I:

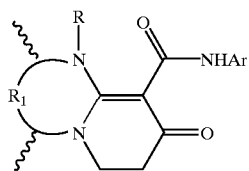

wherein Ar, R and $R_1$ are as hereinafter defined. The compounds of formula I are useful in treating central nervous system disorders. The compounds are ligands for the BZD binding site on GABA-A receptors and are thus useful as muscle relaxants, hypnotics/sedatives including sleep-aids, anxiolytics, anticonvulsants/antiepileptics and antidotes for drug overdose, particularly benzodiazepine overdoses.

DETAILED DESCRIPTION OF THE INVENTION

More particularly, the present invention is directed to compounds of the following formula I

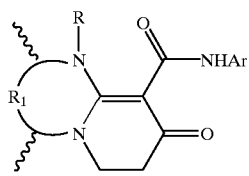

wherein $R_1$ is

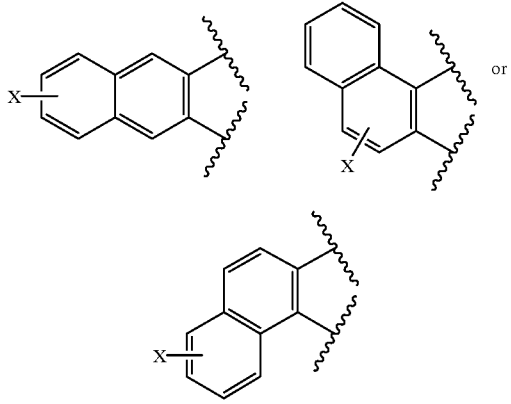

X is selected from one or more of the group consisting of hydrogen, alkyl ($C_1$–$C_8$), branched alkyl ($C_3$–$C_8$), halo, perfluoro(lower alkyl), hydroxy, lower alkoxy, di(lower alkyl) amino, lower alkoxycarbonyl and lower alkylthio; there may be up to six independent substituents on the phenyl ring; X is preferably selected from any of lower alkoxy, hydrogen, halogen and lower alkyl;

R is selected from any of hydrogen, lower alkyl ($C_1$–$C_6$), aralkyl ($C_6$–$C_{10}$), substituted aralkyl ($C_6$–$C_{10}$) (where the phenyl substituents are alkyl ($C_1$–$C_8$), branched alkyl ($C_3$–$C_8$), halo, perfluoro(lower alkyl), hydroxy, lower alkoxy, di(lower alkyl) amino, lower alkoxycarbonyl or lower alkylthio), phenyl, substituted phenyl (where the substituents are alkyl ($C_1$–$C_8$), branched alkyl ($C_3$–$C_8$), halo, perfluoro(lower alkyl), hydroxy, lower alkoxy, di(lower alkyl) amino, lower alkoxycarbonyl or lower alkylthio), ($CH_2$)$_n$$OR_4$ where
n=1–4,
$R_4$ is hydrogen, alkyl ($C_1$–$C_{12}$), cycloalkyl ($C_3$–$C_{10}$), alkoxy ($C_1$–$C_8$), phenyl and substituted phenyl, (where the substituents are alkyl ($C_1$–$C_8$), branched alkyl ($C_3$–$C_8$), halo, perfluoro(lower alkyl), hydroxy, lower alkoxy, di(lower alkyl) amino, mono(lower alkyl)amino, lower alkoxycarbonyl or lower alkylthio, ($CH_2$)$_n$$NR_2R_3$, where n=1–4,
$R_2$ and $R_3$ together or independently are hydrogen, alkyl ($C_1$–$C_{12}$), perfluoro(lower alkyl), cycloalkyl ($C_3$–$C_{10}$), alkoxy ($C_1$–$C_8$), phenyl and substituted phenyl, where the substituents are alkyl ($C_1$–$C_8$), branched alkyl ($C_3$–$C_8$), halo, perfluoro(lower alkyl), hydroxy, lower alkoxy, di(lower alkyl) amino, mono(lower alkyl)amino, lower alkoxycarbonyl and lower alkylthio);

Ar is selected from any of phenyl and substituted phenyl, (where the phenyl substituents are alkyl ($C_1$–$C_8$), branched alkyl ($C_3$–$C_8$), halo, perfluoro(lower alkyl), hydroxy, lower alkoxy, di(lower alkyl) amino, mono (lower alkyl)amino, lower alkoxycarbonyl and lower alkylthio); a heterocycle where the heterocycle is selected from any of pyridine, thiazole, thiophene, furan, indole, pyridazine, pyrimidine, indoline, imidazole, triazine, pyrazine, isoxazole, thiadiazole, triazole and; a substituted heterocycle where the substituents are selected from one or more of halo, perfluoro(lower alkyl), nitro, lower alkylthio, lower alkoxy, lower alkyl, di(lower alkyl) amino, carboxy, lower alkoxycarbonyl,.

As used herein, unless otherwise noted, alkyl and alkoxy whether used alone or as part of a substituent group include straight and branched chains. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, and 3-methylpentyl. Alkoxy radicals are oxygen ethers formed from the previously described straight or branched chain alkyl groups. Halo includes chloro, bromo, fluoro and iodo. Unless otherwise noted, "lower" when used with alkyl and alkoxy means a carbon chain composition of 1–8 carbon atoms. Of course, if the alkyl or alkoxy substituent is branched there must be at least 3 carbons. The term "aralkyl" means a radical containing a lower alkyl group substituted with an aryl radical; the term "aryl" indicates aromatic hydrocarbon groups such as phenyl or napthyl. With reference to substituents, the term independently means that when more than one of such substituents is possible, such substituents may be the same or different from each other.

The definition of formula I as shown in the specification and as used in the claims includes possible isomers, such as tautotmers and rotomers. Also included in the invention are the pharmaceutically acceptable salts, solvates and hydrates thereof.

Examples of particularly preferred compounds of formula I include:

3-oxo-1,2,3,5-tetrahydronaphtho[2',3':4,5]imidazo[1,2-a]pyridine-4-carboxylic acid (2-fluorophenyl)amide (Va, Ar=2-FPh)

3-oxo-1,2,3,5-tetrahydronaphtho[2',3':4,5]imidazo[1,2-a]pyridine-4-carboxylic acid (2,6-difluorophenyl)amide (Vb, Ar=2,6-diFPh)

5-ethyl-3-oxo-1,2,3,5-tetrahydronaphtho[2',3':4,5]imidazo[1,2-a]pyridine-4-carboxylic acid (2-fluorophenyl)amide (VIa, Ar=2-FPh, R=Et)

5-(2-methoxyethyl)-3-oxo-1,2,3,5-tetrahydronaphtho[2',3':4,5]-imidazo[1,2-a]pyridine-4-carboxylic acid (2-fluorophenyl)amide (Ar=2-FPh, R=MeOCH2CH2)

5-[2-(benzylmethylamino)ethyl)-3-oxo-1,2,3,5-tetrahydronaphtho[2', 3':4,5]imidazo[1,2-a]pyridine-4-carboxylic acid (2-fluorophenyl)amide (Ar=2-FPh, R=Bz(Me)NCH2CH2)

5-[2-(benzylmethylamino)ethyl)-3-oxo-1,2,3,5-tetrahydronaphtho[2', 3':4,5]imidazo[1,2-a]pyridine-4-carboxylic acid (2,6-difluorophenyl)amide (Ar=2,6-diFPh, R=Bz(Me)NCH2CH2)

5-[2-(methylamino)ethyl)-3-oxo-1,2,3,5-tetrahydronaphtho[2', 3':4,5]imidazo[1,2-a]pyridine-4-carboxylic acid (2-fluorophenyl)amide hydrochloride (Ar=2-FPh, R=MeNHCH2CH2)

5-[2-(methylamino)ethyl)-3-oxo-1,2,3,5-tetrahydronaphtho-[2', 3':4,5]imidazo[1,2-a]pyridine-4-carboxylic acid (2,6-difluorophenyl)amide hydrochloride (Ar=2,6-diFPh, R=MeNHCH2CH2)

5-Ethoxymethyl-3-oxo-1,2,3,5-tetrahydronaphtho[2', 3':4,5]-imidazo[1,2-a]pyridine-4-carboxylic acid (2,6-difluorophenyl)amide (Ar=2,6-diFPh, R=EtOCH2)

3-Oxo-1,2,3,5-tetrahydronaphtho[2',1':4,5]imidazo[1,2-a]-pyridine-4-carboxylic acid (2-fluorophenylamide) (XIa, Ar=2-FPh, R=H)

5-(2-Methoxyethyl)-3-oxo-1,2,3,5-tetrahydronaphtho[2', 1':4,5]-imidazo[1,2-a]pyridine-4-carboxylic acid (2-fluorophenylamide) (XIb, Ar=2-FPh, R=CH3OCH2CH2) and 3-Oxo-1,2,3,5-tetrahydronaphtho[1',2':4,5]imidazo[1,2-a]pyridine-4-carboxylic acid (2-fluorophenylamide) (XV, Ar=2-FPh, R=H)

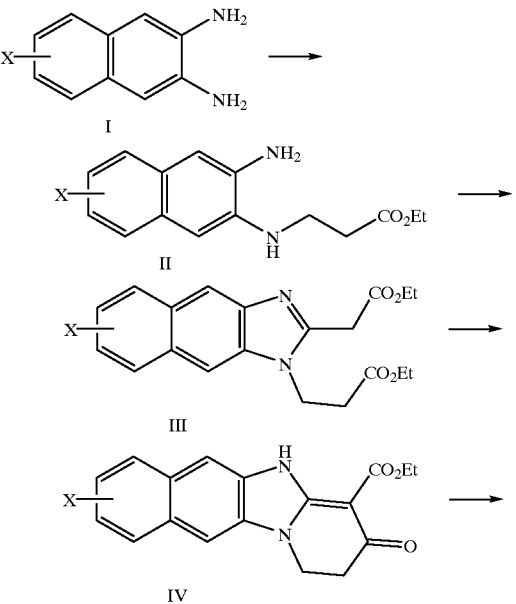

Scheme 1

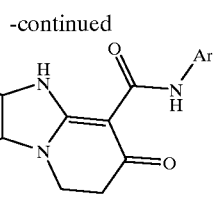

V

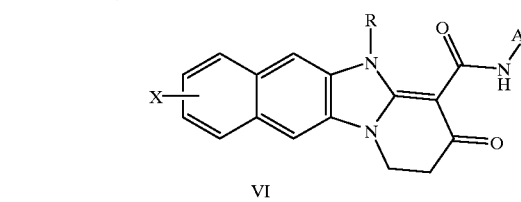

VI

As shown in scheme 1, an appropriately substituted diaminonaphthalene is reacted with a haloalkanoate such as, for example, ethyl 3-bromoproprionate, to form an acid alkyl ester (II). The reaction is carried out at a temperature between room temperature and about 60° C. The product which forms is isolated and purified by techniques known to those skilled in the art. Although the scheme is illustrated with the ethyl ester, it should be understood that the reaction can be carried out with any appropriate haloalkyl ester.

The acid ethyl ester (II) is then reacted with carbethoxy-acetimidate hydrochloride in a suitable solvent such as, for example, ethanol, to form the imidazol propionic acid alkyl ester (III). The reaction is generally carried out at elevated temperatures but preferably at the reflux temperature of the solvent. The resultant crude product is isolated and purified by generally accepted techniques.

The oxo-naphtho-imidazol-pyridine carboxylic acid ester (IV) is prepared by reacting a solution of the imidazol propionic acid alkyl ester (III) with sodium ethoxide, prepared by adding sodium metal spheres to ethanol at room temperature, after which it is poured into a dilute acid such as, for example, dilute hydrochloric acid, and the pH of the resultant solution is adjusted to about neutral (6.5). The product formed is collected and purified by generally accepted techniques.

The carboxylic acid amide (V) is prepared by reacting a mixture of the pyridine carboxylic acid ethyl ester and the appropriately substituted amine (for example 2-aminothiophene, 2-aminopyridine, 4-aminothiazole and the like) in a suitable solvent such as xylene, for example. The reaction is carried out at elevated temperatures but is preferably carried out at the reflux temperature of the solvent. The reaction mixture is cooled to room temperature and the product is collected and purified.

The N-substituted carboxylic acid amide VI is prepared by reacting the carboxylic acid amide V with a substituted azodicarboxylate such as diethyl azodicarboxylate, for example, in the presence of triphenyl phosphine and the appropriate alcohol, in a suitable solvent such as THF, for example. The reaction is carried out at temperatures of about 0° C. The crude product is isolated and purified by techniques known to those skilled in the art.

Scheme 2 illustrates the preparation of the [1',2',4,5] imidazo-[1,2a]pyridine and the [2',1',4,5]imidazo-[1,2-a] pyridine compounds using appropriately substituted starting materials. The difference between Scheme 1 and Scheme 2 is that the first step of Scheme 2 gives two regioisomers, VII and XII. These isomers must be separated by column chromatography on silica gel using appropriate organic solvents before carrying out the remaining steps of the scheme.

Scheme 2

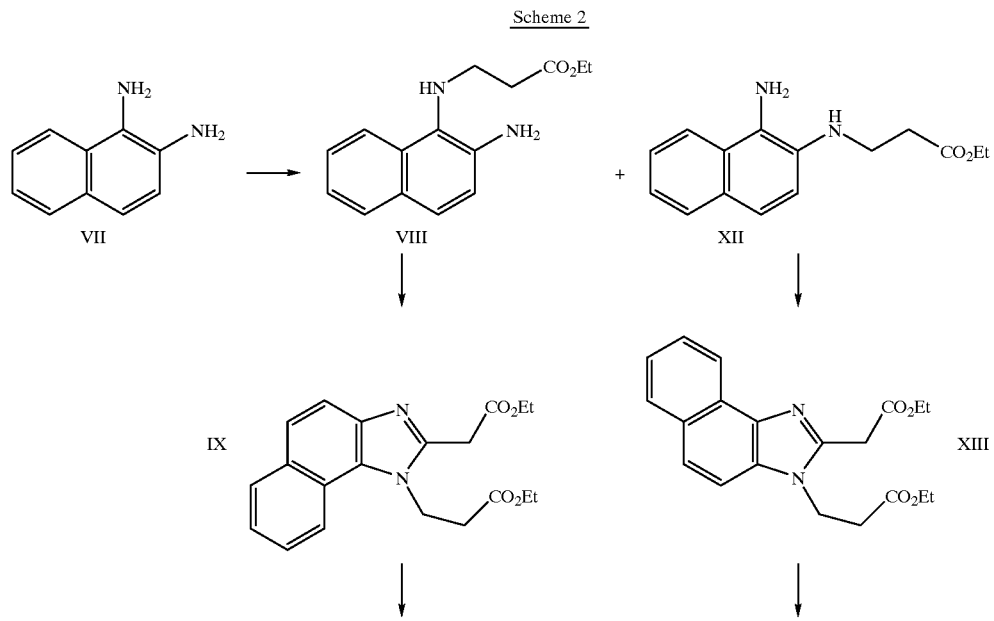

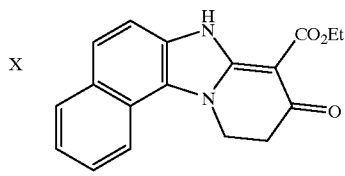

X

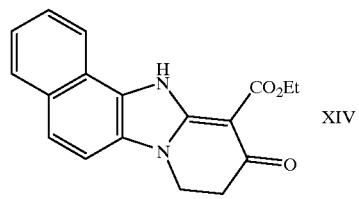

XIV

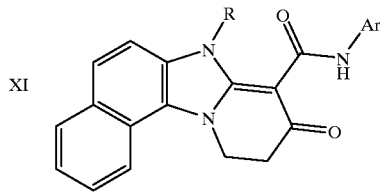

XI

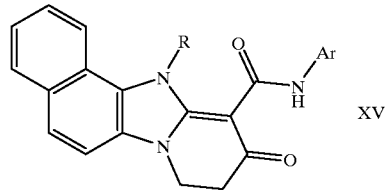

XV

To prepare the pharmaceutical compositions of this invention one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, although other ingredients, for example, for purposes such as aiding solubility or for preservation, may be included. Injectable suspensions may also be prepared in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use in treating disorders of the central nervous system in mammals, the compounds of this invention may be administered in an amount of from about 0.2 to 25 mg/kg per day. In therapeutic use as an anxiolytic, the compounds of the invention may be administered in an amount from about 0.2 to 25 mg/kg per day. In therapeutic use as an anticonvulsant/antiepileptic, the compounds of the invention may be administered in an amount from about 0.2 to about 25 mg/kg per day. In therapeutic use as a sedative/hypnotic, a therapeutically effective amount is from about 0.2 to about 25 mg/kg per day. As a muscle relaxant about 0.2 to 25 mg/kg per day of the compounds of this invention may be used. Determination of optimum dosages for a particular situation is within the skill of the art.

The following examples describe the invention in greater detail and are intended to illustrate the invention, but not to limit it.

Melting point determinations were carried out on a Thomas Hoover or Mel-Temp melting point apparatus and are corrected unless otherwise specified. Each compound has at least two analytical results (elemental analysis, IR, $^1$H NMR, MSS) that are consistent with its assigned structures. The infrared spectra (KBr) were recorded on a Nicolet SX 60 FT spectrometer and are expressed in reciprocal centimeters. Nuclear magnetic resonance (NMR) spectra for hydrogen atoms were measured in the indicated solvent with tetramethylsilane (TMS) as the internal standard on Bruker AM-360 (360 MHz), AM-400 (400 MHz), or AT-300 (300 MHz) spectrometer. The values are expressed in parts per million down field from TMS. The elemental analyses were measured by Atlantic Microlabs (Atlanta, Ga.), Galbraith Labs (Knoxville, Tenn.) or in house and are expressed in percentage by weight of each element per total molecular weight. The mass spectra (MS) were determined on a Finnigan 3300 spectrometer (methane), using desorption chemical ionization techniques. All preparative column chromatography were run using a Waters Prep 500A HPLC (silica gel) employing the appropriate commercially available solvent. Unless otherwise noted, the materials used in the examples were obtained from readily available commercial suppliers or synthesized by standard methods known to anyone skilled in the art of chemical synthesis. The substituent groups, which vary between examples are hydrogen unless otherwise noted.

EXPERIMENTAL 3-(3-Aminonaphthalen-2-ylamino)propionic acid ethyl ester (II)

A solution of 2,3-diaminonaphthalene (14.3 g, 90.4 mmol) and ethyl 3-bromopropionate (14 mL, 0.108 mol) in DMF (150 mL) was heated to 50° C. for 24 h. The reaction mixture was poured into water (600 mL) and the product was extracted into $CH_2Cl_2$ (2×200 mL). The combined organics were washed three times with water and dried over $Na_2SO_4$. The solvent was evaporated in vacuo and the resultant residue was purified by flash chromatography using 27% to 40% EtOAc in hexane as the eluant to give the product as a brown solid, 7.6 g (33%): MS m/z 259 (MH$_+$);

$^1$H NMR (DMSO-d$_6$) δ 1.22 (t, 3H), 2.73 (t, 2H), 3.37–3.45 (m, 2H), 4.12 (q, 2H), 5.03 (br s, 2H), 5.09 (br t, 1H), 6.71 (s, 1H), 6.85 (s, 1H), 6.98–7.05 (m, 2H), 7.36–7.43 (m, 1H) and 7.47–7.53 (m, 1H).

3-(2-Ethoxycarbonylmethylnaphtho[2,3-d]imidazol-1-yl) propionic acid ethyl ester (III). A solution of II (2.6 g, 10.1 mmol) and carbethoxyacetimidate.HCl (2.55 g, 13.8 mmol) in ethanol (50 mL) was heated to reflux for 4 h. The solvent was evaporated in vacuo and the resultant residue was dissolved in CH$_2$Cl$_2$ (200 mL) and washed with saturated aqueous NaHCO$_3$ (200 mL). The organic solution was dried over Na$_2$SO$_4$, and the solvent was evaporated in vacuo. The resultant residue was purified by flash chromatography using 2% to 3% CH$_3$OH in CH$_2$Cl$_2$ as the eluant to give the product as red brown oil, 2.93 (95%), which crystallized upon standing to give a tan solid: mp 82.5–84° C.; MS m/z 355 (MH$_+$); $^1$H NMR (CDCl$_3$) δ 1.21 (t, 3H), 1.28 (t, 3H), 2.97 (t, 2H), 4.13 (q, 2H), 4.20–4.27 (m, 4H), 4.59 (t, 2H), 7.33–7.47 (m, 2H), 7.73 (s, 1H), 7.93–8.03 (m, 2H) and 8.21 (s, 1H).

3-Oxo-1,2,3,5-tetrahydronaphtho[2',3':4,5]imidazo[1,2-a]pyridine-4-carboxylic acid ethyl ester (IV) Sodium metal spheres (1.03 g, 43 mmol) were added to ethanol (30 mL) and stirred at rt until all the sodium was consumed. A solution of III (2.85 g, 8.0 mmol) in ethanol (20 mL) was added to the resultant sodium ethoxide solution and stirred at rt for 2 h. The reaction mixture was poured into a 0.6N HCl (240 mL) and the pH was adjusted to 6.5 with additional 1N HCl. The resultant precipitate was collected by filtration, washed with water and air dried to give an off white solid, 1.76 g (71%): mp 244–248° C.; MS m/z 309 (MH$_+$); $^1$H NMR (CDCl$_3$) δ 1.44 (t, 3H), 2.92 (t, 2H), 4.26 (t, 2H), 4.40 (t, 2H), 7.27 (s, 1H), 7.44–7.54 (m, 3H), 7.67 (s, 1H), 7.87–7.93 (m, 2H) and 11.45 (br s, 1H).

EXAMPLE 1

3-oxo-1,2,3,5-tetrahydronaphtho[2',3':4,5]imidazo[1,2-a]pyridine-4-carboxylic acid (2-fluorophenyl)amide (Va, Ar=2-FPh) A mixture of IV (1.76 g, 5.71 mmol) and 2-fluoroaniline (0.66 mL, 6.85 mmol) in xylenes (50 mL) was heated to reflux for 4 h. The reaction mixture was cooled to rt and the resultant precipitate was collected by filtration. The solid was preabsorbed onto silica gel and purified by flash chromatography using 2% to 5% CH$_3$OH in CH$_2$Cl$_2$ as the eluant to give the product as an off white solid, 1.5 g (70%): mp 265–271° C. (dec); MS m/z 374 (MH$_+$); $^1$H NMR (DMSO-$_6$) 82.89 (t, 2H), 4.38 (t, 2H), 7.00–7.06 (m, 1H), 7.17 (T, 1H), 7.32–7.32 (m, 1H), 7.39–7.50 (m, 3H), 7.94–8.04 (m, 4H), 8.55 (t, 1H), 12.22 (br s, 1H) and 12.72 (br s, 1H).

EXAMPLE 2

3-oxo-1,2,3,5-tetrahydronaphtho[2',3':4,5]imidazo[1,2-a]pyridine-4-carboxylic acid (2,6-difluorophenyl)amide (Vb, Ar=2,6-diFPh) In a similar manner, using 2,6-difluoroaniline, IV (3.0 g, 9.73 mmol) was converted to Vb, a tan solid 2.94 g (77%): 250–253° C. (dec); MS m/z 392 (MH$_+$); $^1$H NMR (DMSO-d$_6$) δ 2.90 (t, 2H), 4.40 (t, 2H), 7.13–7.23 (m, 2H), 7.25–7.37 (m, 1H), 7.40–7.50 (m, 2H), 7.88–8.02 (m, 4H), 11.30 (br s, 1H) and 12.66 (br s, 1H).

EXAMPLE 3

5-ethyl-3-oxo-1,2,3,5-tetrahydronaphtho[2',3':4,5] imidazo[1,2-a]pyridine-4-carboxylic acid (2-fluorophenyl) amide (VIa, Ar=2-FPh, R=Et) Diethyl azodicarboxylate (0.65 mL, 4.82 mmol) was added to a mixture of Va (0.60 g, 1.61 mmol), triphenyl phosphine (1.26 g, 4.82 mmol) and ethanol (0.28 mL, 4.82 mmol) in THF (20 mL) at 0° C. and stirred for 2 h. The solvent was evaporated in vacuo, and the residue was purified by flash chromatography, using 1% CH$_3$OH in CH$_2$Cl$_2$ as the eluant. The product was further purified by recrystallization from isopropanol to give a colorless solid, 0.449 g (69%): mp 233–234° C.; MS m/z402 (MH$_+$); $^1$H NMR (CDCl$_3$) δ 1.50 (t, 3H), 2.87 (t, 2H), 4.23 (t, 2H), 4.58 (q, 2H), 6.94–7.03 (m, 1H), 7.07–7.16 (m, 2H), 7.46–7.54 (m, 2H), 7.60 (s, 1H), 7.78 (s, 1H),7.91–8.00 (m, 2H), 8.50 (dd, 1H) and 12.04 (br s, 1H).

EXAMPLE 4

5-ethyl-3-oxo-1,2,3,5-tetrahydronaphtho[2',3':4,5] imidazo[1,2-a]pyridine-4-carboxylic acid (2,6-difluorophenyl)amide (VIb, Ar=2,6-diFPh. R=Et) In a similar manner, Vb (0.70 g, 1.79 mmol) was converted to VIb 0.318 g (42%), as a colorless solid: mp 236–238° C. (dec); MS m/z 420 (MH$_+$); $^1$H NMR (CDCl$_3$) δ 1.50 (t, 3H), 2.90 (t, 2H), 4.26 (t, 2H), 4.57 (q, 2H), 6.92–7.02 (m, 2H), 7.08–7.19 (m, 1H), 7.47–7.55 (m, 3H), 7.60 (s, 1H), 7.77 (s, 1H), 7.89–7.97 (m, 1H) and 11.31 (br s, 1H).

EXAMPLE 5

5-(2-methoxyethyl)-3-oxo-1,2,3,5-tetrahydronaphtho[2',3':4,5]-imidazo[1,2-a]pyridine-4-carboxylic acid (2-fluorophenyl)amide (Ar=2-FPh. R=MeOCH$_2$CH$_2$) In a similar manner, using 2-methoxyethanol, Va (0.60 g, 1.61 mmol) was converted to example 5, 0.621 g (89%), a colorless solid: mp 213–214° C.; MS m/z 432 (MH$_+$); $^1$H NMR (CDCl$_3$) δ 2.89 (t, 2H), 3.29 (s, 3H), 3.93 (t, 2H), 4.24 (t, 2H), 4.70 (t, 2H), 6.94–7.04 (m, 1H), 7.07–7.16 (m, 2H), 7.46–7.53 (m, 2H), 7.60 (s, 1H), 7.87–7.98 (m, 3H), 8.47 (dd, 1H) and 12.04 (br s, 1H).

EXAMPLE 6

5-[2-(benzylmethylamino)ethyl)-3-oxo-1,2,3,5-tetrahydronaphtho[2',3':4,5]imidazo[1,2-a]pyridine-4-carboxylic acid (2-fluorophenyl)amide (Ar=2-FPh. R=Bz(Me)NCH2CH2) In a similar manner, using 2-(benzymethyamino)ethanol Va (1.5 g, 4.02 mmol) was converted to example 6, a colorless solid, 1.55 g (74%): mp 148–151° C.; $^1$H NMR (CDCl$_3$) δ 2.26 (s, 3H), 2.76–2.87 (m, 4H), 3.43 (s, 2H), 4.20 (t, 2H), 4.68 (t, 2H), 6.92–7.16 (m, 8H), 7.43–7.60 (m, 4H), 7.80–7.94 (m, 2H), 8.49 (dd, 1H) and 12.05 (br s, 1H).

EXAMPLE 7

5-[2-(benzylmethylamino)ethyl)-3-oxo-1,2,3,5-tetrahydronaphtho[2',3':4,5]imidazo[1,2-a]pyridine-4-carboxylic acid (2.6-difluorophenyl)amide (Ar=2,6-diFPh. R=Bz(Me)NCH2CH2) In a similar manner, Vb (1.06 g, 2.71 mmol) was converted to example 7, 1.26 g (86%), a colorless solid: mp 211–214° C.; MS m/z 539 (MH$_+$); $^1$H NMR (CDCl$_3$) δ 2.27 (s, 3H), 2.80–2.88 (m, 4H), 3.41 (s, 2H), 4.22 (t, 2H), 4.69 (t, 2H), 6.93–7.17 (m, 8H), 7.43–7.57 (m, 4H), 7.83 (d, 1H), 7.94 (d, 1H) and 11.36 (br s, 1H).

EXAMPLE 8

5-[2-(methylamino)ethyl)-3-oxo-1,2,3,5-tetrahydronaphtho[2',3':4,5]imidazo[1,2-a]pyridine-4-carboxylic acid (2-fluorophenyl)amide hydrochloride (Ar=2-FPh. R=MeNHCH2CH2) A mixture of example 6 (1.0 g, 1.92 mmol), ammonium formate (1.5 g, 23.7 mmol) and palladium black (50 mg, 0.47 mmol) in ethanol (20 mL) was heated to reflux for 16 h. The catalyst was removed by filtration and the solvent was removed in vacuo. The residue was taken up in $CH_2Cl_2$ (100 mL) and washed with water. The organic solution was dried over $Na_2SO_4$ and the solvent was evaporated in vacuo. The residue was taken up in ethanol (25 mL) and treated with concentrated HCl (1 mL). The product crystallized as the HCl salt as a colorless solid, 0.67 g (75%): mp 236–238° C.; $^1H$ NMR (DMSO-$d_6$) δ 2.51 (s, 3H), 2.83 (t, 2H), 3.53 (br s, 1H), 4.42 (t, 2H), 4.80 (t, 2H), 6.97–7.09 (m, 1H), 7.17 (dd, 1H), 7.28 (dd, 1H), 7.51–7.60 (m, 2H), 7.98–8.09 (m, 2H), 8.16 (s, 1H), 8.40 (s, 1H), 8.54 (dd, 1H), 9.09 (br s, 1H) and 12.33 (br s, 1H).

EXAMPLE 9

5-[2-(methylamino)ethyl)-3-oxo-1,2,3,5-tetrahydronaphtho[2',3':4,5]imidazo[1,2-a]pyridine-4-carboxylic acid (2,6-difluorophenyl)amide hydrochloride (Ar=2,6-diFPh. R=MeNHCH2CH2) In a similar manner, example 7 (0.91 g, 1.69 mmol) was converted to example 9 a colorless solid, 0.127 g (15%): mp 205–207° C.; $^1H$ NMR (DMSO-$d_6$) d 2.53 (s, 3H), 2.84 (t, 2H), 3.47 (br s, 1H), 4.43 (t, 2H), 4.82 (t, 2H), 7.11–7.38 (m, 3H), 7.51–7.68 (m, 2H), 7.98–8.07 (m, 2H), 8.13 (s, 1H), 8.43 (s, 1H), 9.18 (br s, 2H) and 11.57 (br s, 1H).

EXAMPLE 10

5-Ethoxymethyl-3-oxo-1,2,3,5-tetrahydronaphtho[2',3':4,5]-imidazo[1,2-a]pyridine-4-carboxylic acid (2,6-difluorophenyl)amide (Ar=2,6-diFPh. R=EtOCH$_2$) Sodium hydride (60%, 94 mg, 2.34 mmol) was added to a solution of Vb (0.835 g, 2.13 mmol) and 15-crown-5 (catalytic) in DMF (15 mL) at 0° C. and stirred for 1 h. Chloromethyl ethyl ether (0.23 mL, 2.46 mmol) was added to the solution and stirred for 16 h. The reaction mixture was poured into water (100 mL) and the resultant precipitate was collected by filtration washed with water and recrystallized from MeOH to give a colorless solid, 1.72 g (81%): mp 241–232° C. (dec); MS m/z450 (MH$_+$); $^1H$ NMR (CDCl$_3$) δ 1.09 (t, 3H), 2.93 (t, 2H), 3.37 (q, 2H), 4.23 (t, 2H), 5.88 (s, 2H), 6.94–7.03 (m, 2H), 7.10–7.21 (m, 1H), 7.46–7.54 (m, 2H), 7.60 (s, 1H), 7.90–7.97 (m, 3H) and 11.32 (br s, 1H).
1,2-Diaminonaphthalene (VII)

A solution of 1-nitro-2-acetylaminonaphthalene (*J. Amer. Chem. Soc.* 1932, 54, 636) (5.0 g, 24.2 mmol) and concentrated HCl (5 mL) in ethanol (30 mL) was heated to reflux for 4 h. The solvent was evaporated in vacuo, then treated with saturated NaHCO$_3$ (100 mL). The product was extracted into CH$_2$Cl$_2$ (100 mL) and dried over Na$_2$SO$_4$. The solvent was evaporated in vacuo. The residue was dissolved in AcOH, added a catalytic amount of 10% Pd on carbon and hydrogenated at 50 psi H$_2$ for three h. The reaction mixture was concentrated in vacuo and treated with saturated NaHCO$_3$ (100 mL) and extracted with CH$_2$Cl$_2$ (100 mL) and dried over Na$_2$SO$_4$. The solvent was evaporated in vacuo and the residue purified by flash chromatography using 2% CH$_3$OH in CH$_2$Cl$_2$ as the eluant to give the product as a brown solid, 1.9 g (50%): MS m/z 159 (MH$_+$); $^1H$ NMR (CDCl$_3$) δ 3.68 (br s, 4H), 7.03 (d, 1H), 7.23–7.32 (m, 2H), 7.43 (dd, 1H) and 7.68–7.77 (m, 2H).
3-(2-Aminonaphthalen-1-ylamino)propionic acid ethyl ester (VIII) and 3-(1-Amino-naphthalen-2-ylamino)propionic acid ethyl ester (XII)

A solution of VII (11.4 g, 58 mmol) and ethyl 3-bromopropionate (7.5 mL, 58 mmol) in DMF (120 mL) was heated to 50° C. for 8 h. The reaction mixture was poured into water and neutralized with NaHCO$_3$. The products were extracted into CH$_2$Cl$_2$ (2×200 mL). The combined organics were washed with water (4×200 mL) and dried over Na$_2$SO$_4$. The solvent was evaporated in vacuo and the products separated by flash chromatography using 27% EtOAc in hexane as the eluant to give the product VIII, 2.60 g (17%) as a brown solid: MS m/z 259 (MH$_+$); $^1H$ NMR (DMSO-$d_6$) δ 1.22 (t, 3H), 2.64 (t, 2H), 3.09 (br t, 2H), 4.05 (br s, 1H), 4.09 (q, 2H), 5.19 (br s, 2H), 7.04 (d, 1H), 7.13 (dd, 1H), 7.33 (dd, 1H), 7.40 (d, 1H), 7.66 (d, 1H) and 7.97 (d, 1H); and the product XII, 2.06 g (13%) as a brown solid: MS m/z 259 (MH$_+$); H NMR (DMSO-$d_6$) d 1.21 (t, 3H), 2.63 (t, 2H), 3.43 (br m, 2H), 4.10 (q, 2H), 4.65 (br s, 1H), 4.97 (br s, 2H), 7.04 (d, 1H), 7.11–7.18 (m, 2H), 7.27 (dd, 1H), 7.62 (d, 1H), and 7.94 (d, 1H)

3-[2-(Ethoxycarbonylmethyl)naphtho[2,1-d]imidazol-1-yl)propionic acid ethyl ester (IX) In a manner similar to the conversion of II to III, compound VIII (2.60 g, 10.1 mmol) was converted to IX, 1.8 g (50%): MS m/z 355 (MH$_+$); $^1H$ NMR (CDCl$_3$) δ 1.18–1.32 (m, 6H), 3.06 (t, 2H), 4.14–4.27 (m, 6H), 4.92 (t, 2H), 7.50 (dd 1H), 7.62 (dd, 1H), 7.72 (d, 1H), 7.84 (d, 1H), 8.03 (d, 1H), 8.21 (d, 1H).

3-Oxo-1,2,3,5-tetrahydronaphtho[2',1':4,5]imidazo[1,2-a]pyridine-4-carboxylic acid ethyl ester (X) In a manner similar to the conversion of III to IV, compound IX (1.75 g, 4.94 mmol) was converted to X, 1.18 g (78%): MS m/z 309 (MH$_+$); $^1H$ NMR (DMSO-$d_6$) δ 1.27 (t, 3H), 2.69 (t, 2H), 4.22 (q, 2H), 4.85 (t, 2H), 7.53 (dd, 1H), 7.64 (dd, 1H), 7.82 (d, 1H), 7.87 (d, 1H), 8.06 (d, 1H), 8.49 (d, 1H) and 12.64 (br s, 1H).

EXAMPLE 11

3-Oxo-1,2,3,5-tetrahydronaphtho[2',1':4,5]imidazo[1,2-a]-pyridine-4-carboxylic acid (2-fluorophenylamide) (XIa, Ar=2-FPh, R=H). In a manner similar to the conversion of IV to Va, compound X (1.1 g, 3.57 mmol) was converted to the product XIa, 1.13 g (85%) a colorless solid: mp 297–299° C. (dec); MS m/z 374 (MH$_+$); $^1H$ NMR (DMSO-$d_6$) δ 2.87 (t, 2H), 4.95 (t, 2H), 6.97–7.32 (m, 3H), 7.52–7.72 (m, 2H), 7.79–7.95 (m, 2H), 8.08 (d, 1H), 8.49–8.63 (m, 2H), 12.36 (br s, 1H) and 13.08 (br s, 1H).

EXAMPLE 12

5-(2-Methoxyethyl)-3-oxo-1,2,3,5-tetrahydronaphtho[2',1':4,5]-imidazo[1,2-a]pyridine-4-carboxylic acid (2-fluorophenylamide) (XIb, Ar=2-FPh, R=CH3OCH2CH2) Using 2-methoxyethanol, compound XIa (0.63 g, 1.69 mmol) was converted to example 12, a colorless solid: mp 251–253° C. (dec); MS m/z 432 (MH$_+$); $^1H$ NMR (CDCl$_3$) δ 2.87 (t, 2H), 3.26 (s, 3H), 3.87 (t, 2H), 4.79–4.86 (m, 4H), 6.91–6.99 (m, 1H), 7.07–7.16 (m, 2H), 7.60 (dd, 1H), 7.68 (dd, 1H), 7.75–7.84 (m, 2H), 8.03 (d, 1H), 8.32 (d, 1H), 8.57 (dd, 1H) and 12.23 (br s, 1H).

3-[2-(Ethoxycarbonylmethyl)naphtho[1,2-d]imidazol-1-yl)propionic acid ethyl ester (XIII) In a manner similar to the conversion of II to III, compound XII (2.06 g, 7.97 mmol) was converted to XIII, 2.62 g (50%) a brown oil: MS m/z 355 (MH$_+$); $^1H$ NMR (CDCl$_3$) δ 1.21 (t, 3H), 1.30 (t, 3H), 2.94 (t, 2H), 4.13 (q, 2H), 4.17–4.26 (m, 4H), 4.58 (t, 2H), 7.44–7.53 (m, 2H), 7.61 (dd, 1H), 7.72 (d, 1H), 7.93 (d, 1H) and 8.60 (d, 1H).

3-Oxo-1,2,3,5-tetrahydroxynaphtho[1',2':4,5]imidazo[1,2-a]pyridine-4-carboxylic acid ethyl ester (XIV) In a manner similar to the conversion of III to IV, compound XIII (2.62 g, 7.39 mmol) was converted to XIV, 0.65 g (29%) a beige solid: MS m/z309 (MH$_+$); $^1H$ NMR (CDCl$_3$) δ 1.46 (t, 3H), 2.88 (t, 2H), 4.31 (t, 2H), 4.42 (q, 2H), 7.44 (d, 1H), 7.54

(dd, 1H), 7.65 (dd, 1H), 7.79 (d, 1H), 7.97 (d, 1H), 8.04 (d, 1H) and 12.09 br s, 1H).

EXAMPLE 13

3-Oxo-1,2,3,5-tetrahydronaphtho[1',2':4,5]imidazo[1,2-a]pyridine-4-carboxylic acid (2-fluorophenylamide) (XV, Ar=2-FPh, R=H) In a manner similar to the conversion of IV to Va, compound XIV (0.62 g, 2.01 mmol) was converted to example 13, 0.94 9 (47%) a beige solid: mp 297–299° C. (dec); MS m/z374 (MH$_+$); $^1$H NMR (DMSO-d$_6$) δ 2.87 (t, 2H), 4.46 (t, 2H), 6.96–7.07 (m, 1H), 7.18 (dd, 1H), 7.27 (dd, 1H), 7.55 (dd, 1H), 7.67 (dd, 1H), 7.86 (d, 1H), 7.94 (d, 1H), 8.08 (d, 1H), 8.62 (dd, 1H), 8.82 (d, 1H), 12.30 (br s, 1H) and 12.96 (br s, 1H).

glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ value, for all tested compounds is listed in Table 2. An $IC_{50}$ value of over 10,000 for a particular compound indicates that the compound was not active in this screen. This screen is a general screen and

TABLE 1

Physical Properties of Naphthyl Derivatives

| Example # | mp, °C. | C | H | N | empirical formula |
|---|---|---|---|---|---|
| 1 | 265–271 | 70.85 | 4.28 | 11.17 | $C_{22}H_{16}F_2N_3O_2$ |
| 2 | 250–253 | 67.19 | 3.97 | 10.49 | $C_{22}H_{15}F_2N_3O_2$ |
| 3 | 233–234 | 71.92 | 4.93 | 10.29 | $C_{24}H_{20}FN_3O_2$ |
| 4 | 236–238 | 67.92 | 4.54 | 10.02 | $C_{24}H_{19}F_2N_3O_2.0.25H_2O$ |
| 5 | 213–214 | 69.33 | 5.12 | 9.69 | $C_{25}H_{22}FN_3O_3$ |
| 6 | 148–151 | 73.61 | 5.65 | 10.70 | $C_{32}H_{29}FN_4O_2$ |
| 7 | 211–214 | 71.36 | 5.23 | 10.02 | $C_{32}H_{28}F_2N_4O_2$ |
| 8 | 236–238 | 63.91 | 5.13 | 11.80 | $C_{25}H_{23}FN_4O_2.HCl$ |
| 9 | 205–207 | 60.41 | 4.69 | 10.95 | $C_{25}H_{22}F_2N_4O_2.1.1HCl.0.5H_2O$ |
| 10 | 241–242 | 66.44 | 4.64 | 9.38 | $C_{25}H_{21}F_2N_3O_3$ |
| 11 | 297–299 | 70.62 | 4.28 | 11.00 | $C_{22}H_{16}FN_3O_2$ |
| 12 | 251–253 | 69.47 | 5.19 | 9.67 | $C_{25}H_{22}FN_3O_3$ |
| 13 | 278–279 | 70.69 | 4.13 | 11.14 | $C_{22}H_{16}FN_3O_2$ |
| 14 | 215–216 | 72.59 | 5.20 | 9.60 | $C_{26}H_{22}FN_3O_2$ |
| 15 | 238–240 | 69.39 | 5.15 | 9.74 | $C_{25}H_{22}FN_3O_3$ |
| 16 | 221–222 | 67.51 | 4.83 | 10.45 | $C_{22}H_{19}N_5O_2S$ |
| 17 | >275 | 62.71 | 3.76 | 15.37 | $C_{19}H_{14}N_4O_2S$ |
| 18 | 221–222 | 64.55 | 4.71 | 14.22 | $C_{21}H_{18}N_4O_2S$ |
| 19 | 221–222 | 62.83 | 4.90 | 13.20 | $C_{22}H_{20}N_4O_3S$ |
| 20 | 221–222 | 67.28 | 3.83 | 10.60 | $C_{22}H_{15}F_2N_3O_2$ |
| 21 | | 70.27 | 5.25 | 10.02 | $C_{24}H_{20}FN_3O.0.5H_2O$ |
| 22 | | 67.84 | 4.93 | 9.55 | $C_{25}H_{22}FN_3O_3.05H_2O$ |
| 23 | >300 | 67.26 | 3.98 | 10.64 | $C_{22}H_{15}F_2N_3O_2$ |
| 24 | 219.221 | 66.06 | 4.77 | 9.44 | $C_{25}H_{21}F_2N_3O_3.0.25H_2O$ |
| 25 | 215–216 | 65.07 | 5.02 | 8.96 | $C_{26}H_{23}F_2N_3O_3.1H_2O$ |
| 26 | >220 | 66.70 | 4.75 | 9.25 | $C_{25}H_{21}F_2N_3O_3$ |

The compounds of this invention were tested for affinity for the benodiazepine sites of the GABA-A receptor. Since compounds which bind to this receptor can be useful in treating central nervous system disorders, the compounds were also tested in appropriate screens to evaluate specific activities. The results of the various screens are shown in Table 2. Not all compounds were tested in each of the screens. A blank next to a particular compound indicates that the compound was not tested in that screen.

Benzodiazepine Receptor Binding Assay

Selected compounds, which were prepared according to the experimental details given in the following examples, were tested for binding to the benzodiazepine site of the GABA-A receptor (Williams, M. et al., *J. Pharm. Exper. Therap.* 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand (3H-flunitrazepam) was ca. 3 nM. Samples were incubated 10–20 min at 250° C., after which the membrane material and bound ligand was collected on compounds active in this screen are considered active in treating one or more disorders of the central nervous system.

Assay to Determine the Suppression of Metrazol-Induced Convulsions in Adult Male Mice Selected compounds of the invention were tested for their ability to reduce metrazol-induced convulsions in mice (Swinyard, E. A. *J. Am. Pharm Assoc.* 1949, 38, 201). Male $CD_1$ mice, were fasted at least 16 hours, were divided into equal groups and test compounds or vehicle were administered parenterally. Water was not withheld except during the period of observations. At the time of suspected peak activity, anti-pentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 ml/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. 1971. Probit Analysis. London: Cambridge University Press) and are listed in Table 2. An $ED_{50}$ value of greater than 30 indicates that an active dose for the compound being tested had not been determined. Compounds active in this screen are considered active anticonvulsion/antiepileptic agents.

Assay to Measure the Suppression of Anxiety in the Adult Male Rat

The anxiolytic activity of selected compounds of the invention was assessed by determining their ability to release (disinhibit) behavior that had been suppressed by punishment (Vogel, J. R. et al. *Psychopharmacology* 1971, 21, 1). Male rats were deprived of water for 48 hours and were deprived of food for 24 hours prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase (p<0.05, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Tables 1 to 5. The MED was defined as the minimum dose of the drug-treatment as analyzed using the Wilcoxon rank-sum test (SAS; Statistical Analysis System, version 5.16). If the MED value is greater than 10, an active dose of the compound being tested had not been determined.

TABLE 2

Biological activity of Naphthyl derivatives: X=H

| Example # | Ar | R | naphtho-imidazo fusion | $IC_{50}$ nM | anti-metrazol[a] $ED_{50}$ | rat conflict[b] MED |
|---|---|---|---|---|---|---|
| 1 | 2-FPh | H | [2',3':4,5] | 17.0 | 1 | >10 |
| 2 | 2,6-$F_2$Ph | H | [2',3':4,5] | 3.95 | 1 | >10 |
| 3 | 2-FPh | ethyl | [2',3':4,5] | 0.94 | <1 | 10 |
| 4 | 2,6-$F_2$Ph | ethyl | [2',3':4,5] | 6.87 | >1 | >10 |
| 5 | 2-FPh | 2-(methoxy)ethyl | [2',3':4,5] | 0.37 | <1 | 10 |
| 6 | 2-FPh | 2-(N-benzyl-N-methyl amino)ethyl | [2',3':4,5] | 8.02 | >1 | >10 |
| 7 | 2,6-$F_2$Ph | 2-(N-benzyl-N-methyl amino)ethyl | [2',3':4,5] | 58 | >1 | >10 |
| 8 | 2-FPh | 2-(methylamino)-ethyl | [2',3':4,5] | 7.98 | >1 | >10 |
| 9 | 2,6-$F_2$Ph | 2-(methylamino)-ethyl | [2',3':4,5] | 75 | >1 | >10 |
| 10 | 2,6-$F_2$Ph | 2-(ethoxy)methyl | [2',3':4,5] | 13.0 | >1 | >10 |
| 11 | 2-FPh | H | 2',1':4,5] | >1000 | >1 | >10 |
| 12 | 2-FPh | 2-methoxyethyl | [2',1':4,5] | 58 | >1 | >10 |
| 13 | 2-FPh | H | [1',2':4,5] | 154 | >1 | >10 |
| 14 | 2-FPh | (cyclopropyl)methyl | [2',3':4,5] | 0.57 | <1 | >10 |
| 15 | 2-FPh | ethoxymethyl | [2',3':4,5] | 2.18 | <1 | >10 |
| 16 | 2-thineyl | ethyl | [2',3':4,5] | 0.7 | <1 | >10 |
| 17 | 2-thiazoyl | H | [2',3':4,5] | 360 | >1 | |
| 18 | 2-thiazoyl | ethyl | [2',3':4,5] | 11.1 | <1 | >10 |
| 19 | 2-thiazoyl | 2-methoxyethyl | [2',3':4,5] | 3.37 | <1 | >10 |
| 20 | 2,6-$F_2$Ph | H | [1',2':4,5] | 2.73 | <1 | >10 |
| 21 | 2-FPh | ethyl | [1',2':4,5] | 16.5 | >1 | >10 |
| 22 | 2-FPh | 2-methoxyethyl | [1',2':4,5] | 31.8 | >1 | >10 |
| 23 | 2,6-$F_2$Ph | H | [1',2':4,5] | 17.9 | | 10 |
| 24 | 2,6-$F_2$Ph | 2-methoxyethyl | [1',2':4,5] | 0.29 | 1 | >3 |
| 25 | 2,6-$F_2$Ph | 2-ethoxyethyl | [1',2':4,5] | 3.72 | | >3 |
| 26 | 2,6-$F_2$Ph | ethoxymethyl | [1',2':4,5] | 10.3 | | >10 |

[a]ip, mg/kg.
[b]po, mg/kg.

What is claimed is:
1. A compound of the formula:

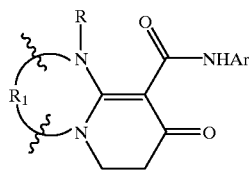

wherein $R_1$ is

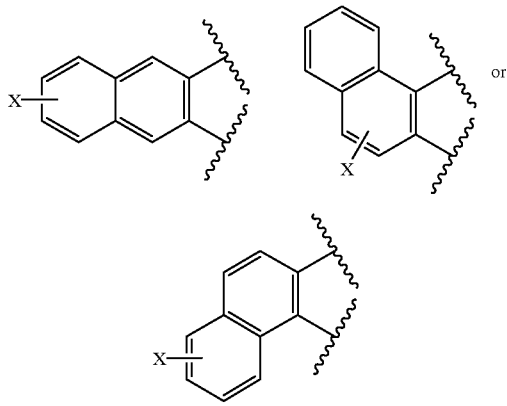

X is selected from one or more of the group consisting of hydrogen, alkyl ($C_1$–$C_8$), branched alkyl ($C_3$–$C_8$), halo, perfluoro(lower alkyl), hydroxy, lower alkoxy, di(lower alkyl) amino, lower alkoxycarbonyl and lower alkylthio; X is selected from the group consisting of lower alkoxy, hydrogen, halogen and lower alkyl;

R is selected from the group consisting of hydrogen, lower alkyl $C_1$–$C_8$), aralkyl ($C_6$–$C_{10}$), substituted aralkyl ($C_6$–$C_{10}$) (where the phenyl substituents are alkyl ($C_1$–$C_8$), branched alkyl ($C_3$–$C_8$), halo, perfluoro (lower alkyl), hydroxy, lower alkoxy, di(lower alkyl) amino, lower alkoxycarbonyl or lower alkylthio), phenyl, substituted phenyl (where the substituents are alkyl ($C_1$–$C_8$), branched alkyl ($C_3$–$C_8$), halo, perfluoro (lower alkyl), hydroxy, lower alkoxy, di(lower alkyl) amino, lower alkoxycarbonyl or lower alkylthio), ($CH_2$)$_n$$OR_4$ where
n=1–4,
$R_4$ is hydrogen, alkyl ($C_1$–$C_{12}$), cycloalkyl ($C_3$–$C_{10}$), alkoxy ($C_1$–$C_8$), phenyl and substituted phenyl, where the substituents are alkyl ($C_1$–$C_8$), branched alkyl ($C_3$–$C_8$), halo, perfluoro(lower alkyl), hydroxy, lower alkoxy, di(lower alkyl) amino, mono(lower alkyl)amino, lower alkoxycarbonyl or lower alkylthio,
($CH_2$)$_n$$NR_2R_3$, where
n=1–4,
$R_2$ and $R_3$ together or independently are hydrogen, alkyl ($C_1$–$C_{12}$), perfluoro(lower alkyl), cycloalkyl ($C_3$–$C_{10}$), alkoxy ($C_1$–$C_8$), phenyl and substituted phenyl, where the substituents are alkyl ($C_1$–$C_8$), branched alkyl ($C_3$–$C_8$), halo, perfluoro(lower alkyl), hydroxy, lower alkoxy, di(lower alkyl) amino, mono(lower alkyl)amino, lower alkoxycarbonyl and lower alkylthio;
Ar is selected from the group consisting of phenyl and substituted phenyl, (where the phenyl substituents are alkyl ($C_1$–$C_8$), branched alkyl ($C_3$–$C_8$), halo, perfluoro (lower alkyl), hydroxy, lower alkoxy, di(lower alkyl) amino, mono(lower alkyl)amino, lower alkoxycarbonyl and lower alkylthio); a heterocycle where the heterocycle is selected from the group consisting of pyridine, thiazole, thiophene, furan, indole, pyridazine, pyrimidine, indoline, imidazole, triazine, pyrazine, isoxazole, thiadiazole, triazole and; a substituted heterocycle where the substituents are selected from one or more of halo, perfluoro(lower alkyl), nitro, lower alkylthio, lower alkoxy, lower alkyl, di(lower alkyl) amino, carboxy, lower alkoxycarbonyl, or a pharmaceutically acceptable salt, solvate, hydrate, tautomer or rotomer thereof.

2. The compound of claim 1 wherein
X is hydrogen, lower alkoxy, halo or lower alkyl;
R is hydrogen, lower alkyl, aralkyl, substituted aralkyl, phenyl, substituted phenyl, ($CH_2$)$_n$$OR_4$ or ($CH_2$)$_n$$NR_2R_3$; and
Ar is phenyl, substituted phenyl, thienyl or thiazoyl.

3. The compound of claim 1 wherein $R_1$ is 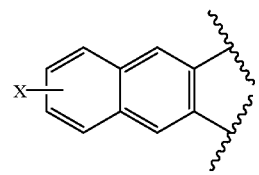 .

4. The compound of claim 1 wherein $R_1$ is 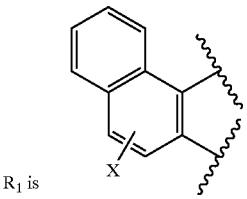 .

5. The compound of claim 1 wherein $R_1$ is 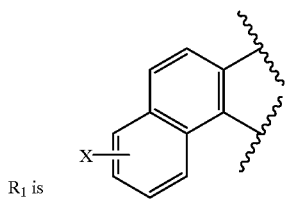 .

6. The compound of claim 1 wherein
X is hydrogen, lower alkoxy, halo or lower alkyl;

$R_1$ is 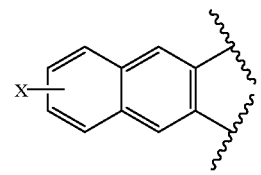 ;

R is hydrogen, lower alkyl, aralkyl, $CH_2$)$_n$$OR_4$ or ($CH_2$)$_n$$NR_2R_3$; and Ar is phenyl, substituted phenyl, thienyl or thiazoyl.

7. The compound of claim 1 wherein

X is hydrogen, lower alkoxy, halo or lower alkyl;

$R_1$ is 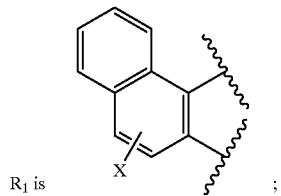;

R is hydrogen, lower alkyl, aralkyl, $(CH_2)_nOR_4$ or $(CH_2)_nNR_2R_3$; and

Ar is phenyl, substitued phenyl, thienyl or thiazoyl.

8. The compound of claim 1 wherein

X is hydrogen, lower alkoxy, halo or lower alkyl;

$R_1$ is 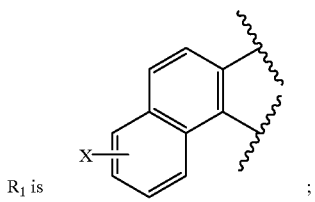;

R is hydrogen, lower alkyl, aralkyl, $(CH_2)_nOR_4$ or $(CH_2)_nNR_2R_3$; and

Ar is phenyl, substituted phenyl, thienyl or thiazoyl.

9. The compound of claim 1 selected from the group consisting of:

3-oxo-1,2,3,5-tetrahydronaphtho[2',3':4,5]imidazo[1,2-a]pyridine-4-carboxylic acid (2-fluorophenyl)amide (Va, Ar=2-FPh)

3-oxo-1,2,3,5-tetrahydronaphtho[2',3':4,5]imidazo[1,2-a]pyridine-4-carboxylic acid (2,6-difluorophenyl)amide (Vb, Ar=2,6-diFPh)

5-ethyl-3-oxo-1,2,3,5-tetrahydronaphtho[2',3':4,5]imidazo[1,2-a]pyridine-4-carboxylic acid (2-fluorophenyl)amide (VIa, Ar=2-FPh, R=Et)

5-(2-methoxyethyl)-3-oxo-1,2,3,5-tetrahydronaphtho[2',3':4,5]-imidazo[1,2-a]pyridine-4-carboxylic acid (2-fluorophenyl)amide (Ar=2-FPh, R=MeOCH$_2$CH$_2$)

5-2-(benzylmethylamino)ethyl-3-oxo-1,2,3,5-tetrahydronaphtho [2',3':4,5]imidazo[1,2-a]pyridine-4-carboxylic acid (2-fluorophenyl)amide (Ar=2-FPh, R=Bz(Me)NCH$_2$CH$_2$)

5-2-(benzylmethylamino)ethyl-3-oxo-1,2,3,5-tetrahydronaphtho [2',3':4,5]imidazo[1,2-a]pyridine-4-carboxylic acid (2,6-difluorophenyl)amide (Ar=2,6-diFPh, R=Bz(Me)NCH$_2$CH$_2$)

5-2-(methylamino)ethyl-3-oxo-1,2,3,5-tetrahydronaphtho[2',3':4,5]imidazo[1,2-a]pyridine-4-carboxylic acid (2-fluorophenyl)amide hydrochloride (Ar=2-FPh, R=MeNHCH$_2$CH$_2$)

5-2-(methylamino)ethyl-3-oxo-1,2,3,5-tetrahydronaphtho[2',3':4,5]imidazo[1,2-a]pyridine-4-carboxylic acid (2,6-difluorophenyl)amide hydrochloride (Ar=2,6-diFPh, R=MeNHCH$_2$CH$_2$)

5-ethoxymethyl-3-oxo-1,2,3,5-tetrahydronaphtho[2',3':4,5]-imidazo[1,2-a]pyridine-4-carboxylic acid (2,6-difluorophenyl)amide (Ar=2,6-diFPh, R=EtOCH$_2$)

3-oxo-1,2,3,5-tetrahydronaphtho[2',1':4,5]imidazo[1,2-a]-pyridine-4-carboxylic acid (2-fluorophenylamide) (XIa, Ar=2-FPh, R=H)

5-(2-methoxyethyl)-3-oxo-1,2,3,5-tetrahydronaphtho [2',1':4,5]-imidazo[1,2-a]pyridine-4-carboxylic acid (2-fluorophenylamide) (XIb, Ar=2-FPh, R=CH$_3$OCH$_2$CH$_2$) and 3-oxo-1,2,3,5-tetrahydronaphtho[1',2':4,5]imidazo[1,2-a] pyridine-4-carboxylic acid (2-fluorophenylamide) (XV, Ar=2-FPh, R=H).

10. A method for treating disorders of the central nervous system comprising administering a compound of the formula I:

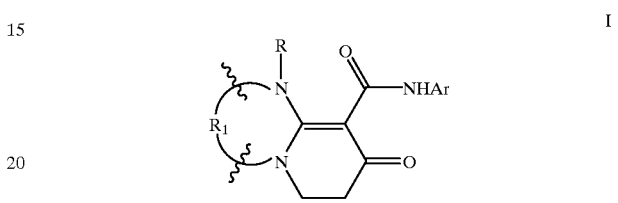

wherein $R_1$ is

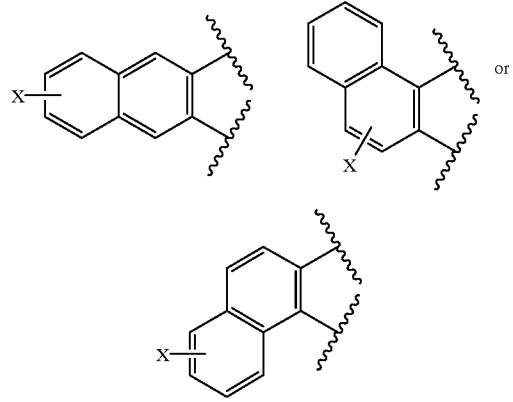

X is selected from one or more of the group consisting of hydrogen, alkyl ($C_1$–$C_8$), branched alkyl ($C_3$–$C_8$), halo, perfluoro(lower alkyl), hydroxy, lower alkoxy, di(lower alkyl) amino, lower alkoxycarbonyl and lower alkylthio; X is selected from the group consisting of lower alkoxy, hydrogen, halogen and lower alkyl;

R is selected from the group consisting of hydrogen, lower alkyl $C_1$–$C_8$), aralkyl ($C_6$–$C_{10}$), substituted aralkyl ($C_6$–$C_{10}$) (where the phenyl substituents are alkyl ($C_1$–$C_8$), branched alkyl ($C_3$–$C_8$), halo, perfluoro (lower alkyl), hydroxy, lower alkoxy, di(lower alkyl) amino, lower alkoxycarbonyl or lower alkylthio), phenyl, substituted phenyl (where the substituents are alkyl ($C_1$–$C_8$), branched alkyl ($C_3$–$C_8$), halo, perfluoro (lower alkyl), hydroxy, lower alkoxy, di(lower alkyl) amino, lower alkoxycarbonyl or lower alkylthio), $(CH_2)_nOR_4$ where n=1–4, $R_4$ is hydrogen, alkyl ($C_1$–$C_{12}$), cycloalkyl ($C_3$–$C_{10}$), alkoxy ($C_1$–$C_8$), phenyl and substituted phenyl, where the substituents are alkyl ($C_1$–$C_8$), branched alkyl ($C_3$–$C_8$), halo, perfluoro(lower alkyl), hydroxy, lower alkoxy, di(lower alkyl) amino, mono(lower alkyl)amino, lower alkoxycarbonyl or lower alkylthio, (CH$_2$)$_n$NR$_2$R$_3$, where
n=1–4,
R$_2$ and R$_3$ together or independently are hydrogen, alkyl (C$_1$–C$_{12}$), perfluoro(lower alkyl), cycloalkyl (C$_3$–C$_{10}$), alkoxy (C$_1$–C$_8$), phenyl and substituted phenyl, where the substituents are alkyl (C$_1$–C$_8$), branched alkyl (C$_3$–C$_8$), halo, perfluoro(lower alkyl), hydroxy, lower alkoxy, di(lower alkyl) amino, mono(lower alkyl)amino, lower alkoxycarbonyl and lower alkylthio;

Ar is selected from the group consisting of phenyl and substituted phenyl, (where the phenyl substituents are alkyl (C$_1$–C$_8$), branched alkyl (C$_3$–C$_8$), halo, perfluoro (lower alkyl), hydroxy, lower alkoxy, di(lower alkyl) amino, mono(lower alkyl)amino, lower alkoxycarbonyl and lower alkylthio); a heterocycle where the heterocycle is selected from the group consisting of pyridine, thiazole, thiophene, furan, indole, pyridazine, pyrimidine, indoline, imidazole, triazine, pyrazine, isoxazole, thiadiazole, triazole and; a substituted heterocycle where the substituents are selected from one or more of halo, perfluoro(lower alkyl), nitro, lower alkylthio, lower alkoxy, lower alkyl, di(lower alkyl) amino, carboxy, lower alkoxycarbonyl, or a pharmaceutically acceptable salt, solvate, hydrate, tautomer or rotomer thereof, to a mammal afflicted with a disorder of the central nervous system in an amount effective for treating such disorder.

11. The method of claim 10 wherein the effective amount is from about 5 to about 500 mg/kg per dose.

12. The method of claim 10 wherein the disorder is anxiety.

13. The method of claim 10 wherein the disorder is convulsions.

14. The method of claim 10 wherein the disorder is sleeplessness.

15. The method of claim 10 wherein the disorder is muscle spasm.

16. The method of claim 10 wherein the disorder is benzodiazepine drug overdose.

17. A pharmaceutical composition comprising a compound of formula I:

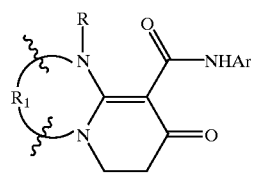

wherein R$_1$ is

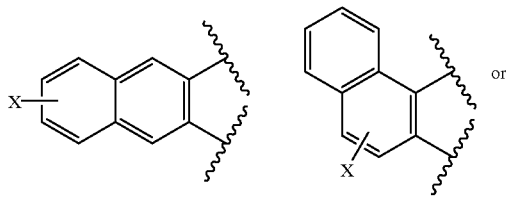

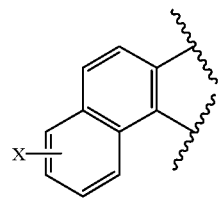

X is selected from one or more of the group consisting of hydrogen, alkyl (C$_1$–C$_8$), branched alkyl (C$_3$–C$_8$), halo, perfluoro(lower alkyl), hydroxy, lower alkoxy, di(lower alkyl) amino, lower alkoxycarbonyl and lower alkylthio; X is selected from the group consisting of lower alkoxy, hydrogen, halogen and lower alkyl;

R is selected from the group consisting of hydrogen, lower alkyl
C$_1$–C$_8$), aralkyl (C$_6$–C$_{10}$), substituted aralkyl (C$_6$–C$_{10}$) (where the phenyl substituents are alkyl (C$_1$–C$_8$), branched alkyl (C$_3$–C$_8$), halo, perfluoro(lower alkyl), hydroxy, lower alkoxy, di(lower alkyl) amino, lower alkoxycarbonyl or lower alkylthio), phenyl, substituted phenyl (where the substituents are alkyl (C$_1$–C$_8$), branched alkyl (C$_3$–C$_8$), halo, perfluoro (lower alkyl), hydroxy, lower alkoxy, di(lower alkyl) amino, lower alkoxycarbonyl or lower alkylthio),
(CH$_2$)$_n$OR$_4$ where
n=1–4,
R$_4$ is hydrogen, alkyl (C$_1$–C$_{12}$), cycloalkyl (C$_3$–C$_{10}$), alkoxy (C$_1$–C$_8$), phenyl and substituted phenyl, where the substituents are alkyl (C$_1$–C$_8$), branched alkyl (C$_3$–C$_8$), halo, perfluoro(lower alkyl), hydroxy, lower alkoxy, di(lower alkyl) amino, mono(lower alkyl)amino, lower alkoxycarbonyl or lower alkylthio,
(CH$_2$)$_n$NR$_2$R$_3$, where
n=1–4,
R$_2$ and R$_3$ together or independently are hydrogen, alkyl (C$_1$–C$_{12}$), perfluoro(lower alkyl), cycloalkyl (C$_3$–C$_{10}$), alkoxy (C$_1$–C$_8$), phenyl and substituted phenyl, where the substituents are alkyl (C$_1$–C$_8$), branched alkyl (C$_3$–C$_8$), halo, perfluoro(lower alkyl), hydroxy, lower alkoxy, di(lower alkyl) amino, mono(lower alkyl)amino, lower alkoxycarbonyl and lower alkylthio;

Ar is selected from the group consisting of phenyl and substituted phenyl, (where the phenyl substituents are alkyl (C$_1$–C$_8$), branched alkyl (C$_3$–C$_8$), halo, perfluoro (lower alkyl), hydroxy, lower alkoxy, di(lower alkyl) amino, mono(lower alkyl)amino, lower alkoxycarbonyl and lower alkylthio); a heterocycle where the heterocycle is selected from the group consisting of pyridine, thiazole, thiophene, furan, indole, pyridazine, pyrimidine, indoline, imidazole, triazine, pyrazine, isoxazole, thiadiazole, triazole and; a substituted heterocycle where the substituents are selected from one or more of halo, perfluoro(lower alkyl), nitro, lower alkylthio, lower alkoxy, lower alkyl, di(lower alkyl) amino, carboxy, lower alkoxycarbonyl, or a pharmaceutically acceptable salt, solvate, hydrate, tautomer or rotomer thereof
in an amount effective for treating disorders of the central nervous system and a pharmaceutically acceptable carrier or diluent.

* * * * *